United States Patent
Komine et al.

(10) Patent No.: US 6,834,551 B2
(45) Date of Patent: Dec. 28, 2004

(54) HYDRAULIC SERVO-TYPE MATERIAL TESTING APPARATUS

(75) Inventors: Noriaki Komine, Kyoto (JP);
Mitsuhiko Araki, 80-2
Kamigamo-Azekatsu-cho, Kita-ku,
Kyoto-shi, Kyoto-fu (JP), 603-8044;
Hidefumi Taguchi, 4-8-13-303
Shibahara-cho, Toyonaka-shi, Osaka-fu
(JP), 560-0055

(73) Assignees: Shimadzu Corporation, Kyoto (JP);
Mitsuhiko Araki, Kyoto (JP);
Hidefumi Taguchi, Toyonaka (JP)

( * ) Notice: Subject to any disclaimer, the term of this patent is extended or adjusted under 35 U.S.C. 154(b) by 0 days.

(21) Appl. No.: 10/260,490

(22) Filed: Sep. 30, 2002

(65) Prior Publication Data

US 2003/0084730 A1 May 8, 2003

(30) Foreign Application Priority Data

Sep. 28, 2001 (JP) ........................ 2001-302570

(51) Int. Cl.[7] .............................. G01N 3/00
(52) U.S. Cl. .................................... 73/798
(58) Field of Search ................ 73/798, 796, 794, 73/788

(56) References Cited

U.S. PATENT DOCUMENTS

| | | | | |
|---|---|---|---|---|
| 3,664,179 A | * | 5/1972 | Danko et al. ................ | 73/579 |
| 4,056,974 A | * | 11/1977 | Klinger et al. ............... | 73/797 |
| 4,354,224 A | * | 10/1982 | Sato ........................... | 700/78 |
| 4,691,576 A | * | 9/1987 | Schleuniger et al. ......... | 73/821 |
| 4,718,281 A | * | 1/1988 | Crews, Jr. .................... | 73/794 |
| 5,245,528 A | * | 9/1993 | Saito et al. .................. | 700/41 |
| 5,408,591 A | * | 4/1995 | Shih et al. ................... | 358/1.5 |
| 5,865,512 A | * | 2/1999 | Meiser et al. ............... | 303/139 |
| 6,098,465 A | * | 8/2000 | Matsumoto et al. ......... | 73/808 |
| 6,205,863 B1 | * | 3/2001 | Ishii et al. ................... | 73/805 |

FOREIGN PATENT DOCUMENTS

JP  58-72204  4/1983

OTHER PUBLICATIONS

Journal of Guangdong University of Technology, vol. 15 Supplement, Apr. 1998.

* cited by examiner

*Primary Examiner*—Edward Lefkowitz
*Assistant Examiner*—Takisha Miller
(74) *Attorney, Agent, or Firm*—Rankin, Hill, Porter & Clark LLP

(57) ABSTRACT

An adjusting unit in a feedback loop for controlling a hydraulically operated-type load mechanism consists of two portions both adapted to effect proportional action and derivative action. Weights are applied to these two portions independently. Hence, an output y can be made to follow sudden changes in a target value r with fast response without the occurrence of overshoots, and the effect of a disturbance input w is alleviated to a maximum. In addition, since integral action is not effected in the adjusting portions, the term of $1/s^2$ is not included in transfer functions of inputs and outputs, thereby realizing stability of control.

9 Claims, 4 Drawing Sheets

HYDRAULIC SERVO-TYPE MATERIAL TESTING APPARATUS

BACKGROUND OF THE INVENTION

1. Field of the Invention

The present invention relates to a hydraulic servo-type material testing apparatus.

2. Description of the Related Art

In a hydraulic servo-type material testing apparatus, generally, a load mechanism for applying a load to a test piece is driven by a hydraulic actuator. A target value concerning a physical value selected as a controlled variable is supplied from a waveform generator or the like. At the same time, the load according to the target value is applied to the test piece by feeding back a detected value of that controlled variable. For example, the physical value selected as the controlled variable is a displacement of the load mechanism, the load applied to the test piece in consequence of that displacement, or the like.

In the hydraulic servo-type material testing apparatus having such a feedback loop, so-called PID control is conventionally performed in which a deviation obtained by feeding back a detected value to a target value is subjected to proportional-integration-derivative (PID) operations so as to obtain a manipulated variable. To show an example of the configuration of its control system, as shown in FIG. 3, the arrangement provided is such that a detected value (observed variable) obtained by detecting a physical quantity selected as a controlled variable z, such as the displacement of the load mechanism, the load applied to the test piece or the like is fed back to a target value r outputted from such as a waveform generator 31. Then, its deviation e is introduced to a PID adjuster 33 to perform proportional-integration-derivative operations, thereby obtaining a manipulated variable u for changing a valve opening of a servo valve 34, so as to control the driving of a hydraulic actuator 35 for the load mechanism. It should be noted that w denotes a disturbance. Specifically, variations in the hydraulic pressure, the wear of a seal portion of the hydraulic actuator, and the like are conceivable as the disturbances.

This control system is shown more specifically in the block diagram of FIG. 4.

In FIG. 4, reference numeral 1 denotes a proportional element; Kp, a proportional gain; $T_I$, integral time; 1/s, an integral element; $T_D$, derivative time; D(s), a derivative element; and P(s), a transfer characteristic of a controlled system.

Incidentally, with the conventional hydraulic servo-type material testing apparatus adopting the above-described PID control, there is a problem in that it is difficult to optimize both the target value response and the disturbance response.

Namely, if, as shown in FIG. 5A, adjustment is made in which the response to the target value is optimized, the response to a disturbance becomes large, as shown in FIG. 5B. On the other hand, if, as shown in FIG. 6B, optimum adjustment is made so that the response to the disturbance becomes small, the response to the target value becomes inordinately large, as shown in FIG. 6A.

In addition, in the conventional hydraulic servo-type material testing apparatus adopting the PID control, the integral element 1/s is included in the transfer characteristic P(s) of a hydraulic drive system, which is the controlled system, as well as the integral element 1/s in an adjusting unit. Therefore, the term of $1/s^2$ is included in the transfer functions of inputs and outputs. Hence, there is a problem in that control becomes unstable, and in an extreme case there is a possibility of the occurrence of hunting.

SUMMARY OF THE INVENTION

The invention has been devised in view of the above-described circumstances, and its object is to provide a hydraulic servo-type material testing apparatus which is capable of optimizing both the target value response and the disturbance response, and of stabilizing the control.

To attain the above object, in accordance with the invention, there is provided a hydraulic servo-type material testing apparatus having a feedback loop for controlling a hydraulically operated-type load mechanism which applies a load to a material, the apparatus comprising an adjusting unit in the feedback loop, the adjusting unit having a first portion for effecting a proportional action and a derivative action with respect to a target value and a second portion for effecting a proportional action and a derivative action with respect to a detected value.

In the hydraulic servo-type material testing apparatus, it is preferable that parameters for the proportional actions and derivative actions of the first and second portions are independently set.

Further, it is preferable that the parameters are a weight to be applied to the first portion and a weight to be applied to the second portion.

In the invention, the fact that the first and second portions of the adjusting unit in the feedback loop both effect proportional action and derivative action means that proportional elements and derivative elements function in the first and second portions of the adjusting unit. Accordingly, as for integral elements, the invention includes both a configuration in which the integral elements are absent in the adjusting unit and a configuration in which even if they are present, the integral time is set to be long to such an extent that they substantially do not function.

In the invention, the adjusting unit in the feedback loop effects proportional action and derivative action, and does not effect integral action. Namely, by substantially adopting PD control, the term of $1/s^2$ is eliminated from the transfer functions of inputs and outputs of the system. At the same time, the adjusting unit consists of a first portion acting with respect to a target value and a second portion acting with respect to a detected value. By setting parameters for the proportional actions and the derivative actions of the first and second portions independently, especially, applying weights to the first and second portions independently, optimization adjustment of both the target value response and the disturbance response is realized.

Namely, in the hydraulic servo-type material testing apparatus, since 1/s is included in the transfer characteristics of the hydraulically-operated load mechanism, which is the controlled system, if the integral element 1/s were made to function in the adjusting unit, the term of $1/s^2$ would be included in the transfer functions of inputs and outputs. In the invention, however, since the integral elements are not made to function in the adjusting unit, the term of $1/s^2$ is not included in the transfer functions of inputs and outputs, thereby making it possible to eliminate a factor for instability of control.

In addition, the first portion acting with respect to the target value and the second portion acting with respect to the detected value are provided separately in the adjusting unit, and arbitrary parameters, especially, weights are respectively applied to these portions. The smaller the weight for the first portion is, the sharper changes in outputs can be suppressed even if there occur sudden changes in the inputs of the target value, thereby making it possible to suppress the occurrence of overshoots. Nevertheless, the rise of outputs becomes slow. On the other hand, if the proportional gain which is equally applied to both of the first and second portions is made large, the feedback is reinforced and disturbances are controlled more powerfully. However, if the proportional gain is made excessively large, the system becomes oscillatory and becomes unstable. For these reasons, by performing a simulation in advance, the weight, which is to be applied to the first portion acting with respect to the target value, of the two portions of the adjusting unit, and the value of the proportional gain are appropriately adjusted, and the value for controlling the disturbance is determined and set in a state that sharp changes will not occur in the outputs and the system does not become oscillatory. It is thereby possible to realize a control system which is capable of controlling disturbances powerfully and in which sharp changes do not occur in the outputs. Consequently, it is possible to obtain a control system which is able to simultaneously obtain the target value response such as the one shown in FIG. 5A and the disturbance response such as the one shown in FIG. 6B.

DETAILED DESCRIPTION OF THE INVENTION

Figure 1:
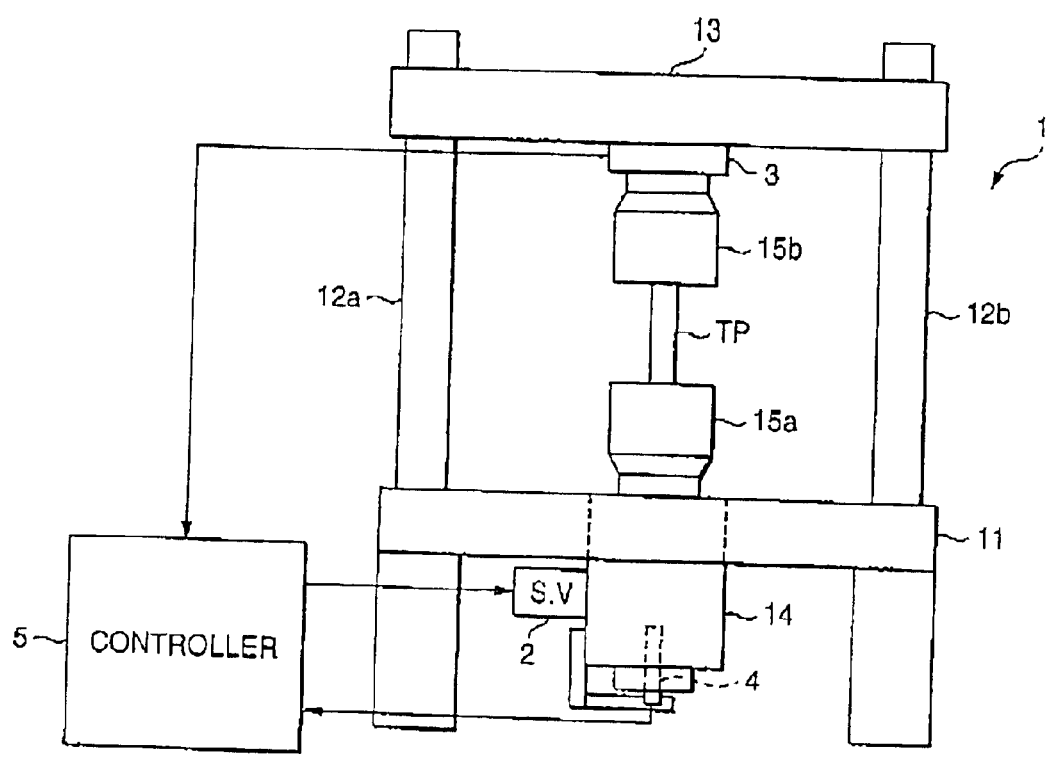
FIG. 1 is a schematic diagram of an apparatus in accordance with an embodiment of the invention.

Referring now to the drawings, a description will be given of an embodiment of the invention.

Figure 2:
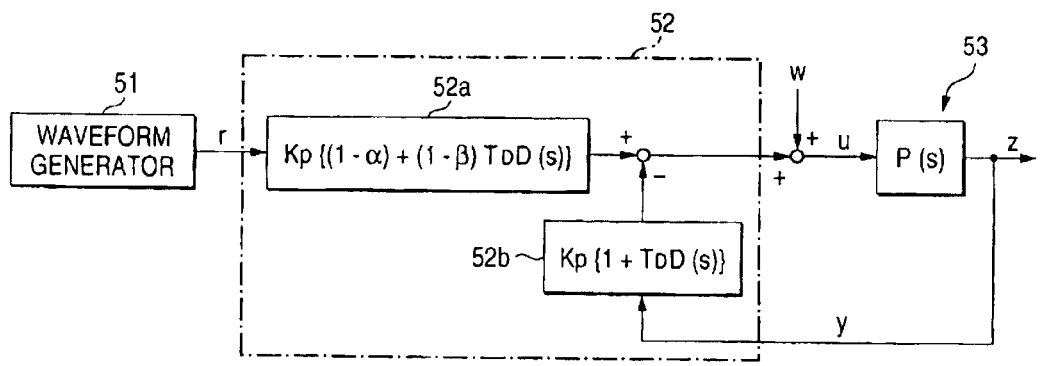
FIG. 2 is a block diagram illustrating the detailed configuration of a control system in accordance with the invention.
Figure 3:
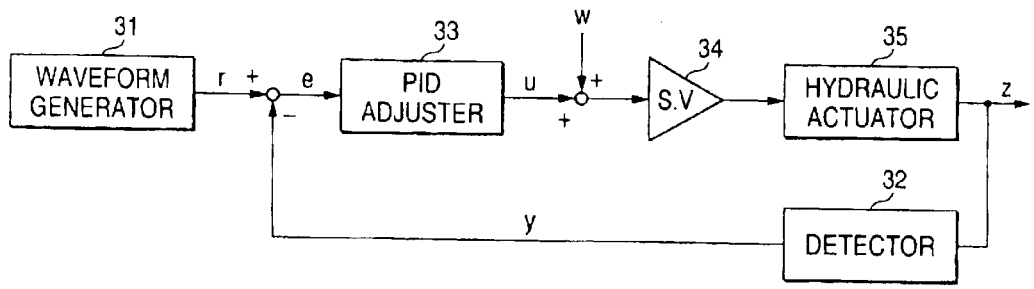
FIG. 3 is a block diagram illustrating an example of the configuration of a control system of a conventional hydraulic servo-type material testing apparatus.
Figure 4:
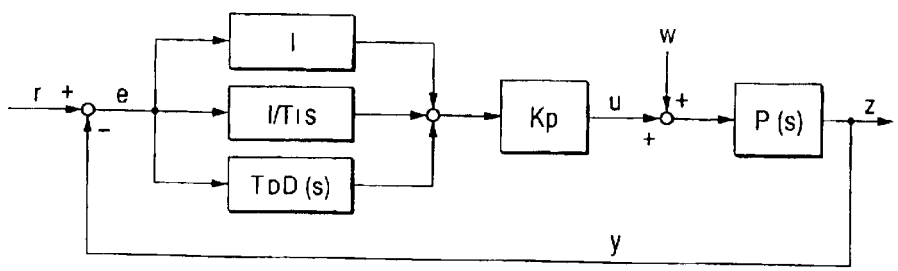
FIG. 4 is a block diagram illustrating the details of a control system shown in FIG. 3.

FIG. 1 is a schematic diagram of the apparatus in accordance with an embodiment of the invention, and FIG. 2 is a block diagram illustrating the detailed configuration of its control system.

A testing apparatus body 1 has a structure in which two columns 12a and 12b are provided on a table 11, and both end portions of a cross yoke 13 are supported by the columns 12a and 12b.

A load mechanism 14, in which a hydraulic cylinder operated by pressure oil supplied thereto through a servo valve 2 is used as an actuator, is provided on the table 11. A lower gripper 15a is fitted on this load mechanism 14, while an upper gripper 15b is fitted to the aforementioned cross yoke 13 through a load cell 3. A test piece TP is used in the test in a state in which its both ends are gripped by the upper and lower grippers 15a and 15b.

Namely, as for the test piece TP whose both ends are gripped by the upper and lower grippers 15a and 15b, a load is applied thereto by the driving of the load mechanism 14, the load applied to the test piece TP is detected by the load cell 3, and the displacement of the load mechanism 14 is detected by a displacement gage 4.

Detected signals of the load and the displacement detected respectively by the load cell 3 and the displacement gage 4 are consecutively fetched into a controller 5. The controller 5 stores consecutive outputs from the load cell 3 and the displacement gage 4 as test data. The controller 5 includes a waveform generator 51 for outputting a target value r and an adjusting unit 52, as shown in FIG. 2. A detected signal representing a physical quantity selected as a controlled variable z, such as the load detected by the load cell 3, is set as a detected value (observed variable) y and is introduced to the adjusting unit 52 so as to structure a feedback loop. Then, a manipulated variable u to be supplied to a controlled system 53 is generated.

The characteristic of this control system lies in that the adjusting unit 52 is formed by a first adjusting portion 52a acting with respect to the target value r and a second adjusting portion 52b acting with respect to the detected value y, and an arbitrary weight $(1-\alpha)$ can be applied to a proportional element of the first adjusting portion 52a while an arbitrary weight $(1-\beta)$ can also be applied to a derivative element of that adjusting portion 52a. These two adjusting portions 52a and 52b include a proportional gain $K_p$ and derivative time $T_D$, which are the same parameters as those included in a conventional PD adjuster. Since the structure is such that the aforementioned four parameters can be arbitrarily set and applied, it is possible to independently set all the magnitudes concerning the proportional action and the derivative action with respect to the target value r, as well as the proportional action and the derivative action with respect to the detected value y. Consequently, an operational advantage is offered in that it is possible to optimally set both the target value response and the disturbance response, as will be described later.

In the above-described embodiment, since both first and second adjusting portions 52a and 52b constituting the adjusting unit 52 do not effect the integral action, the term concerning the integral element included in transfer functions of inputs and outputs of the entire system is only the term of the integral element 1/s included in the hydraulically-operated load mechanism 14, which is the controlled system. Therefore, the term of $1/s^2$ which is included in the conventional hydraulic servo-type material testing apparatus is not included in the hydraulic servo-type material testing apparatus of the present invention. Accordingly, it is possible to eliminate the instability of control.

In addition, in the above-described embodiment, if the parameters $\alpha$ and $\beta$ in the first adjusting portion 52a acting with respect to the target value r are made large, i.e., if weights of the proportional element and the derivative element with respect to the target value r are made small, sharp changes in the output y at the time of sudden changes in the target value r become small, thereby making it possible to suppress the occurrence of overshoots, although the rise becomes slow. On the other hand, if the proportional gain Kp which is equally applied to the overall elements is made large, it is possible to control disturbances more powerfully, but if it is made excessively large, the system becomes oscillatory and becomes unstable. Accordingly, by performing a simulation in advance, such a combination of parameters that the disturbance controlling capability becomes most powerful is determined within the range in which the delay in the rise is small and overshoots do not occur and within the range that the system does not become oscillatory. The setting of the adjusting unit 52 is effected by using these values. Consequently, it is possible to obtain the target value response in an optimal state such as the one shown in FIG. 5A.

Figure 5A:
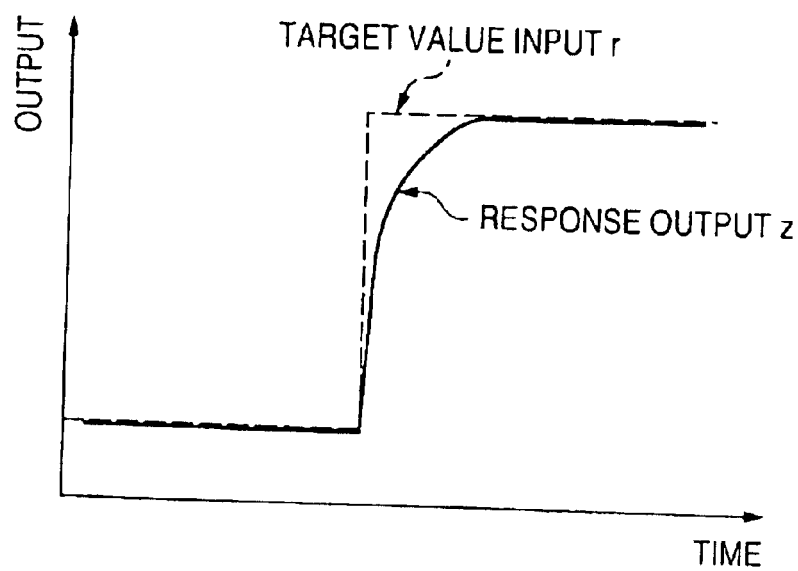
FIG. 5A is a graph illustrating the target value response at the time of an adjustment in which the target value response is optimized in a conventional hydraulic servo-type material testing apparatus adopting the PID control.
Figure 5B:
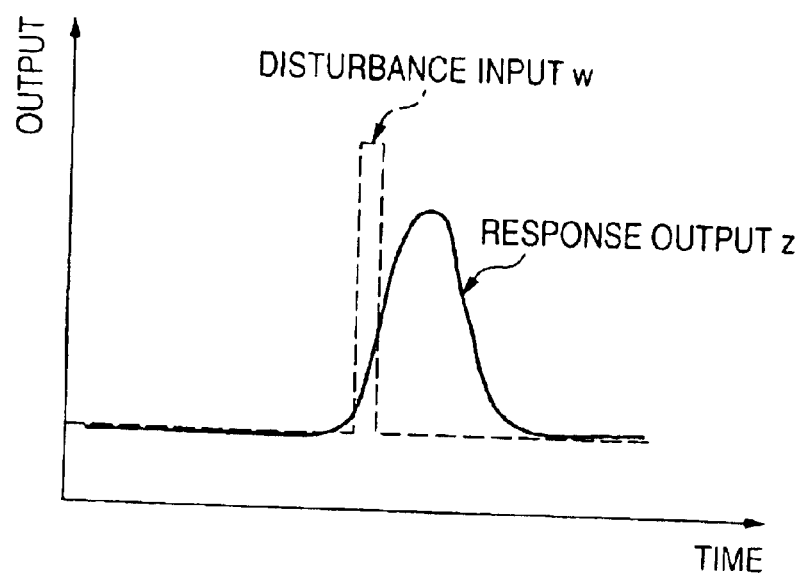
FIG. 5B is a graph illustrating the disturbance response at the time of the adjustment in which the target value response is optimized in the conventional hydraulic servo-type material testing apparatus adopting the PID control.
Figure 6A:
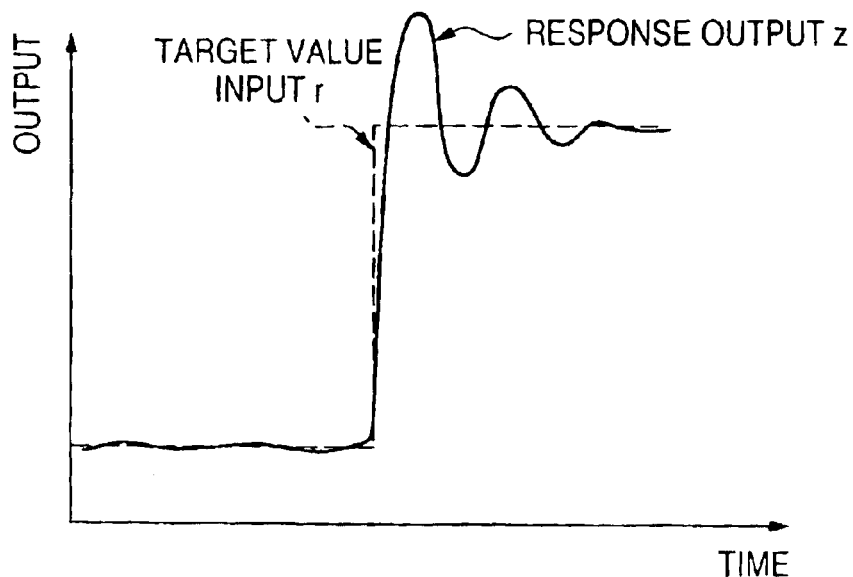
FIG. 6A is a graph similarly illustrating the target value response at the time of an adjustment in which the disturbance response is optimized in the conventional hydraulic servo-type material testing apparatus adopting the PID control.
Figure 6B:
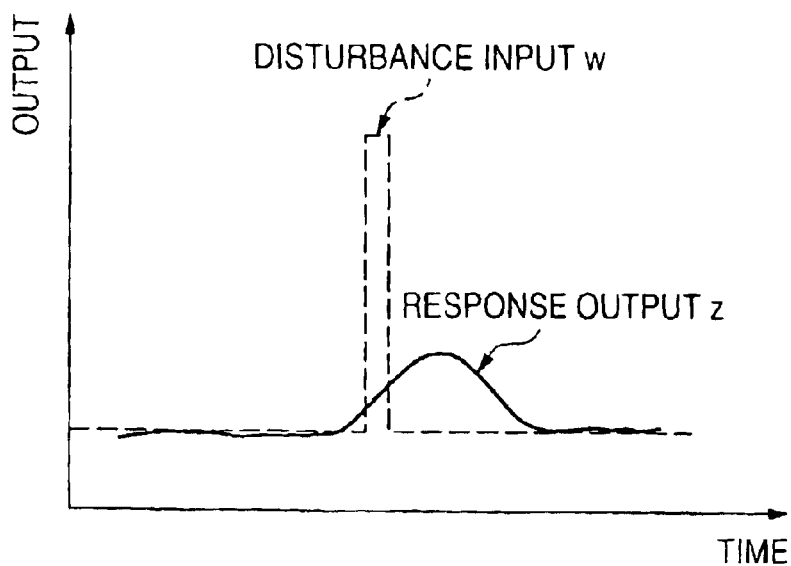
FIG. 6B is a graph similarly illustrating the disturbance response at the time of the adjustment in which the disturbance response is optimized in the conventional hydraulic servo-type material testing apparatus adopting the PID control.

Moreover, in the state in which the target value response is adjusted to the optimal state such as the one shown in FIG. 5A, it is possible to suppress the effect of a disturbance input w. With respect to the disturbance response as well, it is thus possible to obtain it in an optimal state such as the one shown in FIG. 6B.

It should be noted that although the block diagram shown in FIG. 2 is expressed by a collection of blocks representing the functions of the respective portions, it goes without saying that the circuit configuration for attaining these functions may be arranged such that analog circuits corresponding to the respective blocks are provided, or software for executing the functions of the respective blocks may be provided by using a computer.

In addition, although the block diagram shown in FIG. 2 in the foregoing description is expressed by a general equation model of a two-degree-of-freedom control system, this block diagram can be expressed equivalently by a feedforward model, a loop compensation model, a feedback compensation model, a target value filter model, or an element separation model. It goes without saying that the difference in the method of its expression is irrelevant to the gist of the invention. The invention includes all models which adopt the two-degree-of-freedom PD control which can be applied to the hydraulic servo-type material testing apparatus.

Further, although in the adjusting unit as shown in FIG. 2, the arbitrary weight (1−α) and the arbitrary weight (1−β) are applied to the proportional element and the derivative element of the first adjusting portion 52a, theses arbitrary weights can be applied to the proportional and derivative elements of the second adjusting portion 52b.

As described above, in accordance with the invention, the adjusting unit of the hydraulic servo-type material testing apparatus includes two portions which effect proportional action and derivative action and do not effect integral action. The two portions separately effect the actions with respect to a target value and a detected value, respectively. The weights are applied to these two portions independently. Therefore, even if the term of 1/s of an integral element is included in the transfer functions of the hydraulically operated-type load mechanism itself, which is the controlled system, the term of $1/s^2$ is not included in the transfer functions of inputs and outputs, which has not been the case with the conventional art, thereby making it possible to eliminate the instability of control. At the same time, by appropriately setting the weights, with respect to sudden changes in the input of the target value it is possible to obtain outputs in which the rise is sharp and which is free of overshoots, while with respect to the input of a disturbance it is possible to provide control excelling in the controlling capability. Therefore, it possible to maximize both the target value response and the disturbance response.

What is claimed is:

1. A hydraulic servo-type material testing apparatus having a feedback loop for controlling a hydraulically operated-type load mechanism which applies a load to a material, the apparatus comprising:

an adjusting unit in said feedback loop, the adjusting unit having a first portion for effecting a proportional action and a derivative action with respect to a target value and a second portion for effecting a proportional action and a derivative action with respect to a detected value.

2. The hydraulic servo-type material testing apparatus according to claim 1, wherein parameters for the proportional actions and derivative actions of the first and second portions are independently set.

3. The hydraulic servo-type material testing apparatus according to claim 2, wherein the parameters are a weight to be applied to the first portion and a weight to be applied to the second portion.

4. The hydraulic servo-type material testing apparatus according to claim 2, wherein the parameters are a proportional gain for the proportional actions and a derivative time for the derivative actions of the first and second portions, and a weight to be applied to the proportional action and a weight to be applied to the derivative action of the first portion.

5. The hydraulic servo-type material testing apparatus according to claim 1, wherein an output of the second portion is introduced to an output of the first portion.

6. The hydraulic servo-type material testing apparatus according to claim 1, wherein said adjusting unit further comprises a comparator that compares an output of said first portion with an output of said second portion and generates a manipulated variable therefrom, the manipulated variable being used to control said apparatus.

7. The hydraulic servo-type material testing apparatus according to claim 6, wherein parameters for the proportional actions and derivative actions of the first and second portions are independently set.

8. The hydraulic servo-type material testing apparatus according to claim 7, wherein the parameters are a weight to be applied to the first portion and a weight to be applied to the second portion.

9. The hydraulic servo-type material testing apparatus according to claim 7, wherein the parameters are a proportional gain for the proportional actions and a derivative time for the derivative actions of the first and second portions, and a weight to be applied to the proportional action and a weight to be applied to the derivative action of the first portion.

* * * * *